(12) United States Patent
Goupil et al.

(10) Patent No.: US 7,070,809 B2
(45) Date of Patent: *Jul. 4, 2006

(54) HYDROGEL BIOMEDICAL ARTICLES

(75) Inventors: Dennis W. Goupil, Norcross, GA (US); Hassan Chaouk, Atlanta, GA (US); Troy Holland, Suwanee, GA (US); Bruktawit T. Asfaw, Atlanta, GA (US); Stephen D. Goodrich, Norcross, GA (US); Lucas Latini, Norcross, GA (US)

(73) Assignee: BioCure, Inc., Norcross, GA (US)

( * ) Notice: Subject to any disclaimer, the term of this patent is extended or adjusted under 35 U.S.C. 154(b) by 279 days.

This patent is subject to a terminal disclaimer.

(21) Appl. No.: 09/805,483

(22) Filed: Mar. 13, 2001

(65) Prior Publication Data

US 2001/0056301 A1    Dec. 27, 2001

Related U.S. Application Data

(60) Provisional application No. 60/188,975, filed on Mar. 13, 2000.

(51) Int. Cl.
*A61K 9/14* (2006.01)

(52) U.S. Cl. ............ 424/489; 424/499; 424/501; 424/422; 424/424; 514/772

(58) Field of Classification Search ............ 424/422, 424/423, 489, 501; 514/772, 772.1, 772.2
See application file for complete search history.

(56) References Cited

U.S. PATENT DOCUMENTS

| | | | |
|---|---|---|---|
| 4,863,972 A * | 9/1989 | Itagaki et al. ............ 521/141 |
| 5,047,055 A | 9/1991 | Bao | |
| 5,202,352 A | 4/1993 | Okada et al. | |
| 5,344,452 A | 9/1994 | Lemperle | |
| 5,410,016 A | 4/1995 | Hubbell | |
| 5,508,317 A | 4/1996 | Muller | |
| 5,514,379 A | 5/1996 | Weissleder | |
| 5,529,914 A | 6/1996 | Hubbell et al. | |
| 5,879,713 A | 3/1999 | Roth | |
| 5,902,599 A | 5/1999 | Anseth | |
| 5,932,674 A | 8/1999 | Muller | |
| 5,981,826 A | 11/1999 | Ku et al. | |
| 6,028,164 A | 2/2000 | Loomis | |
| 6,060,534 A | 5/2000 | Ronan | |
| 6,083,524 A | 7/2000 | Sawhney et al. | |
| 6,153,211 A | 11/2000 | Hubbell et al. | |
| 6,162,844 A * | 12/2000 | Lally et al. ............ 523/106 |
| 6,166,130 A | 12/2000 | Rhee | |
| 6,191,193 B1 | 2/2001 | Lee et al. | |
| 6,201,065 B1 | 3/2001 | Pathak | |
| 6,265,509 B1 * | 7/2001 | Muller ............ 526/266 |

FOREIGN PATENT DOCUMENTS

| | | |
|---|---|---|
| EP | 730 847 | 11/1996 |
| WO | WO 92/21327 | 12/1992 |
| WO | WO 99/12577 | 3/1999 |
| WO | WO 99/44643 | 9/1999 |
| WO | WO 00/09088 | 2/2000 |
| WO | WO 00/23054 | 4/2000 |
| WO | WO 00/09190 | 8/2000 |
| WO | WO 00/45868 | 8/2000 |
| WO | WO 00/50103 | 8/2000 |
| WO | WO 01/55360 | 2/2001 |
| WO | WO 01/17574 | 3/2001 |
| WO | WO 01/44307 | 6/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | WO 01/72281 | 10/2001 |
| WO | WO 02/16443 | 2/2002 |

OTHER PUBLICATIONS

Kinoshita et al., Neuroradiology 36:65-68 (1994).
Nishi S. et al., ASAIO Journal M405-M410 (1998).
Thanoo BC et al., J. Appl. Biomater. 2:67-72 (1991).
Thanoo BC et al., J. Pharm. Pharmacol. 45:16-20 (1993).
Zou YH, Zhonghua Fang Xue Za Zhi, 23(6):330-2 (1989).

* cited by examiner

*Primary Examiner*—Thurman K. Page
*Assistant Examiner*—Lakshmi Channavajjala
(74) *Attorney, Agent, or Firm*—Collen A. Beard

(57) ABSTRACT

Hydrogel biomedical articles formed from macromers having a polymeric backbone comprising 1,2-diol and/or 1,3-diol units, such as polyvinyl alcohol, and pendant chains bearing crosslinkable groups and, optionally, other modifiers.

9 Claims, No Drawings

HYDROGEL BIOMEDICAL ARTICLES

RELATED APPLICATIONS

This application claims priority to U.S. Ser. No. 60/188,975, filed on Mar. 13, 2000.

BACKGROUND OF THE INVENTION

The invention relates to biomedical articles. More specifically, the invention relates to hydrogel biomedical articles formed from crosslinkable macromonomers (referred to herein as macromers).

Poly(vinyl alcohol) (PVA) hydrogels have been proposed as medical devices, however many of the proposed devices have suffered either from inferior mechanical strength or from tissue damage resulting from the use of chemical agents to harden them. To overcome this problem, Tanabe (U.S. Pat. No. 4,734,097) and Ku (U.S. Pat. No. 5,981,826) have proposed the use of cryogels. However these cryogels are not covalently crosslinked and hence are not suitable for long-term contact with tissues and cannot be formed in vivo. Bao (U.S. Pat. No. 5,047,055) proposes the use of PVA hydrogels as a prosthetic nucleus for a vertebral disc but he also does not form these hydrogels by covalent crosslinking, rather he crystallizes a solution of PVA at a temperature of −10° C. or below. Nambu (U.S. Pat. No. 4,808,353) makes artificial biological membranes of PVA solutions by a similar freezing process. Capecchi (U.S. Pat. No. 5,108,428) describes UV cured PVA hydrogel cornea implants, but these are first pressed into sheets at 191° C. for two minutes and then solvolyzed in 10% methanolic ammonium hydroxide before final application.

SUMMARY OF THE INVENTION

The invention relates to hydrogel biomedical articles formed from macromers having a polymeric backbone comprising units having a 1,2-diol and/or 1,3-diol structure. Such polymers include polyhydroxy polymers such as poly(vinyl alcohol) (PVA) and hydrolyzed copolymers of vinyl acetate, for example, copolymers with vinyl chloride, N-vinylpyrrolidone, etc. The backbone polymer contains pendant chains bearing crosslinkable groups and, optionally, other modifiers. When crosslinked, the macromers form hydrogels having many properties advantageous for use as biomedical articles.

A wide variety of biomedical articles can be made, such as, but not limited to, catheters, tubing, such as neural regeneration tubing, vascular grafts, heart valves, sutures, prostheses, dialysis membranes, filters, sensors, wound dressings, and drug delivery articles. The hydrogel forms all or a portion of the biomedical articles. For example, the hydrogel can form a coating on the article.

Methods for making hydrogel biomedical articles are also provided using the crosslinkable macromers. The methods involve dissolving the macromers in solution and crosslinking the macromers to form the desired article. The macromer solution may be free formed into the article, formed onto a substrate, or a mold may be used. Crosslinking of the macromers is generally accomplished by exposing the macromers to a crosslinking initiator. This can be done after the macromer solution is formed into the desired shape or before or during the shaping.

DETAILED DESCRIPTION OF THE INVENTION

The invention relates to hydrogel biomedical articles made from macromers having a backbone of a polyhydroxy polymer and having at least two pendant chains including a crosslinkable group and optionally other pendant chains containing modifiers.

The hydrogel biomedical articles can be produced very simply and efficiently due to a number of factors. Firstly, the starting materials, such as the polyhydroxy polymer backbones, are inexpensive to obtain or prepare. Secondly, the macromers are stable, so that they can be subjected to very substantial purification. The crosslinking can therefore be carried out using a macromer that is highly pure, containing substantially no unpolymerized constituents. Furthermore, the crosslinking can be carried out in purely aqueous solutions. Aldehyde is not required.

I. The Macromers

The Macromer Backbone

The macromers have a backbone of a polymer comprising units having a 1,2-diol or 1,3-diol structure, such as a polyhydroxy polymer. For example, polyvinyl alcohol (PVA) or copolymers of vinyl alcohol contain a 1,3-diol skeleton. The backbone can also contain hydroxyl groups in the form of 1,2-glycols, such as copolymer units of 1,2-dihydroxyethylene. These can be obtained, for example, by alkaline hydrolysis of vinyl acetate-vinylene carbonate copolymers. Other polymeric diols can be used, such as saccharides.

In addition, the macromers can also contain small proportions, for example, up to 20%, preferably up to 5%, of comonomer units of ethylene, propylene, acrylamide, methacrylamide, dimethacrylamide, hydroxyethyl methacrylate, alkyl methacrylates, alkyl methacrylates which are substituted by hydrophilic groups, such as hydroxyl, carboxyl or amino groups, methyl acrylate, ethyl acrylate, vinylpyrrolidone, hydroxyethyl acrylate, allyl alcohol, styrene, polyalkylene glycols, or similar comonomers usually used.

Polyvinyl alcohols that can be used as macromer backbones include commercially available PVAs, for example Vinol® 107 from Air Products (MW 22,000 to 31,000, 98 to 98.8% hydrolyzed), Polysciences 4397 (MW 25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®), Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the macromer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the macromer backbones are polyvinyl acetates, Mowilith 30 from Hoechst is particularly suitable.

Poly(vinyl alcohols) that can be derivatized as described herein preferably have a molecular weight of at least about 2,000. As an upper limit, the PVA may have a molecular weight of up to 1,000,000. Preferably, the PVA has a molecular weight of up to 300,000, especially up to approximately 130,000, and especially preferably up to approximately 60,000.

The PVA usually has a poly(2-hydroxy)ethylene structure. The PVA derivatized in accordance with the disclosure may, however, also comprise hydroxy groups in the form of 1,2-glycols.

The PVA system can be a fully hydrolyzed PVA, with all repeating groups being —$CH_2$—CH(OH), or a partially hydrolyzed PVA with varying proportions (1% to 25%) of pendant ester groups. PVA with pendant ester groups have repeating groups of the structure $CH_2$—CH(OR) where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (2000 to 4000) PVA.

The PVA is prepared by basic or acidic, partial or virtually complete hydrolysis of polyvinyl acetate. In a preferred embodiment, the PVA comprises less than 50% of vinyl acetate units, especially less than about 25% of vinyl acetate units. Preferred amounts of residual acetate units in the PVA, based on the sum of vinyl alcohol units and acetate units, are approximately from 3 to 25%.

Crosslinkable Groups

The macromers have at least two pendant chains containing groups that can be crosslinked. The term group includes single polymerizable moieties, such as an acrylate, as well as larger crosslinkable regions, such as oligomeric or polymeric regions. The crosslinkers are desirably present in an amount of from approximately 0.01 to 10 milliequivalents of crosslinker per gram of backbone (meq/g), more desirably about 0.05 to 1.5 meq/g. The macromers can contain more than one type of crosslinkable group.

The pendant chains are attached via the hydroxyl groups of the backbone. Desirably, the pendant chains having crosslinkable groups are attached via cyclic acetal linkages to the 1,2-diol or 1,3-diol hydroxyl groups.

Crosslinking of the macromers may be via any of a number of means, such as physical crosslinking or chemical crosslinking. Physical crosslinking includes, but is not limited to, complexation, hydrogen bonding, desolvation, Van der wals interactions, and ionic bonding. Chemical crosslinking can be accomplished by a number of means including, but not limited to, chain reaction (addition) polymerization, step reaction (condensation) polymerization and other methods of increasing the molecular weight of polymers/oligomers to very high molecular weights. Chain reaction polymerization includes, but is not limited to, free radical polymerization (thermal, photo, redox, atom transfer polymerization, etc.), cationic polymerization (including onium), anionic polymerization (including group transfer polymerization), certain types of coordination polymerization, certain types of ring opening and metathesis polymerizations, etc. Step reaction polymerizations include all polymerizations which follow step growth kinetics including but not limited to reactions of nucleophiles with electrophiles, certain types of coordination polymerization, certain types of ring opening and metathesis polymerizations, etc. Other methods of increasing molecular weight of polymers/oligomers include but are not limited to polyelectrolyte formation, grafting, ionic crosslinking, etc.

Various crosslinkable groups are known to those skilled in the art and can be used, according to what type of crosslinking is desired. For example, hydrogels can be formed by the ionic interaction of divalent cationic metal ions (such as $Ca^{+2}$ and $Mg^{+2}$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. Multifunctional cationic polymers, such as poly(l-lysine), poly(allylamine), poly(ethyleneimine), poly(guanidine), poly(vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. Block and graft copolymers of water soluble and insoluble polymers exhibit such effects, for example, poly(oxyethylene)-poly(oxypropylene) block copolymers, copolymers of poly(oxyethylene) with poly(styrene), poly(caprolactone), poly(butadiene), etc.

Solutions of other synthetic polymers such as poly(N-alkylacrylamides) also form hydrogels that exhibit thermoreversible behavior and exhibit weak physical crosslinks on warming. A two component aqueous solution system may be selected so that the first component (among other components) consists of poly(acrylic acid) or poly(methacrylic acid) at an elevated pH of around 8–9 and the other component consists of (among other components) a solution of poly(ethylene glycol) at an acidic pH, such that the two solutions on being combined in situ result in an immediate increase in viscosity due to physical crosslinking.

Other means for polymerization of the macromers also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in some of the macromers of the composition. In this case, no external initiators of polymerization are needed and polymerization proceeds spontaneously when two complementary reactive functional groups containing moieties interact at the application site.

Desirable crosslinkable groups include (meth)acrylamide, (meth)acrylate, styryl, vinyl ester, vinyl ketone, vinyl ethers, etc. Particularly desirable are ethylenically unsaturated functional groups.

Ethylenically unsaturated groups can be crosslinked via free radical polymerization, including via photoinitiation, redox initiation, and thermal initiation. Systems employing these means of initiation are well known to those skilled in the art. In one embodiment, a two part redox system is employed. One part of the system contains a reducing agent such as a ferrous salt. Various ferrous salts can be used, such as, for example, ferrous gluconate dihydrate, ferrous lactate dihydrate, or ferrous acetate. The other half of the solution contains an oxidizing agent such as hydrogen peroxide. Either or both of the redox solutions can contain macromer, or it may be in a third solution. The two solutions are combined to initiate the crosslinking.

Other reducing agents can be used, such as, but not limited to, cuprous salts, cerous salts, cobaltous salts, permanganate, and manganous salts. Ascorbate, for example, can be used as a coreductant to recycle the reductant and reduce the amount needed. This can reduce the toxicity of a ferrous based system. Other oxidizing agents that can be used include, but are not limited to, t-butyl hydroperoxide, t-butyl peroxide, benzoyl peroxide, cumyl peroxide, etc.

Specific Macromers

Specific macromers that are suitable for use in forming the hydrogel biomedical articles are disclosed in U.S. Pat.

Nos. 5,508,317, 5,665,840, 5,807,927, 5,849,841, 5,932,674, 5,939,489, and 6,011,077.

In one embodiment, units containing a crosslinkable group conform, in particular, to the formula I

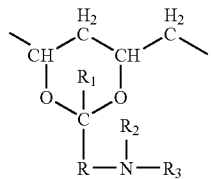

in which R is a linear or branched $C_1$–$C_8$ alkylene or a linear or branched $C_1$–$C_{12}$ alkane. Suitable alkylene examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The groups ethylene and butylene are especially preferred. Alkanes include, in particular, methane, ethane, n- or isopropane, n-, sec- or tert-butane, n- or isopentane, hexane, heptane, or octane. Preferred groups contain one to four carbon atoms, in particular one carbon atom.

$R_1$ is hydrogen, a $C_1$–$C_6$ alkyl, or a cycloalkyl, for example, methyl, ethyl, propyl or butyl and $R_2$ is hydrogen or a $C_1$–$C_6$ alkyl, for example, methyl, ethyl, propyl or butyl. $R_1$ and $R_2$ are preferably each hydrogen.

$R_3$ is an olefinically unsaturated electron attracting copolymerizable radical having up to 25 carbon atoms. In one embodiment, $R_3$ has the structure

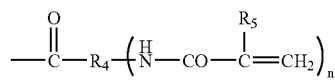

where $R_4$ is the

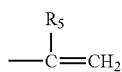

group if n=zero, or the

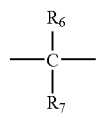

bridge if n=1;

$R_5$ is hydrogen or $C_1$–$C_4$ alkyl, for example, n-butyl, n- or isopropyl, ethyl, or methyl;

n is zero or 1, preferably zero; and $R_6$ and $R_7$, independently of one another, are hydrogen, a linear or branched $C_1$–$C_8$ alkyl, aryl or cyclohexyl, for example one of the following: octyl, hexyl, pentyl, butyl, propyl, ethyl, methyl, 2-propyl, 2-butyl or 3-pentyl. $R_6$ is preferably hydrogen or the $CH_3$ group, and $R_7$ is preferably a $C_1$–$C_4$ alkyl group. $R_6$ and $R_7$ as aryl are preferably phenyl.

In another embodiment, $R_3$ is an olefinically unsaturated acyl group of formula $R_8$—CO—, in which $R_8$ is an olefinically unsaturated copolymerizable group having from 2 to 24 carbon atoms, preferably from 2 to 8 carbon atoms, especially preferably from 2 to 4 carbon atoms. The olefinically unsaturated copolymerizable radical $R_8$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The groups ethenyl and 2-propenyl are preferred, so that the group —CO—$R_8$ is the acyl radical of acrylic or methacrylic acid.

In another embodiment, the group $R_3$ is a radical of formula

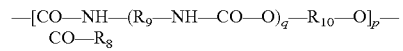

wherein p and q are zero or one and $R_9$ and $R_{10}$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and $R_8$ is as defined above.

Lower alkylene $R_9$ or $R_{10}$ preferably has from 2 to 6 carbon atoms and is especially straight-chained. Suitable examples include propylene, butylene, hexylene, dimethylethylene and, especially preferably, ethylene.

Arylene $R_9$ or $R_{10}$ is preferably phenylene that is unsubstituted or is substituted by lower alkyl or lower alkoxy, especially 1,3-phenylene or 1,4-phenylene or methyl-1,4-phenylene.

A saturated divalent cycloaliphatic group $R_9$ or $R_{10}$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_9$ or $R_{10}$ is preferably phenylene, unsubstituted or substituted by lower alkyl or lower alkoxy, and the alkylene unit thereof is preferably lower alkylene, such as methylene or ethylene, especially methylene. Such radicals $R_9$ or $R_{10}$ are therefore preferably phenylenemethylene or methylenephenylene.

Arylenealkylenearylene $R_9$ or $R_{10}$ is preferably phenylene-lower alkylene-phenylene having up to 4 carbon atoms in the alkylene unit, for example phenyleneethylenephenylene.

The radicals $R_9$ and $R_{10}$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylene-phenylene.

The group —$R_9$—NH—CO—O— is present when q is one and absent when q is zero. Macromers in which q is zero are preferred.

The group —CO—NH—($R_9$—NH—CO—O)$_q$—$R_{10}$-O— is present when p is one and absent when p is zero. Macromers in which p is zero are preferred.

In macromers in which p is one, q is preferably zero. Macromers in which p is one, q is zero, and $R_{10}$ is lower alkylene are especially preferred.

All of the above groups can be monosubstituted or polysubstituted, examples of suitable substituents being the following: $C_1$–$C_4$ alkyl, such as methyl, ethyl or propyl, —COOH, —OH, —SH, $C_1$–$C_4$ alkoxy (such as methoxy, ethoxy, propoxy, butoxy, or isobutoxy), —$NO_2$, —$NH_2$, —NH($C_1$–$C_4$), —NH—CO—$NH_2$, —N($C_1$–$C_4$ alkyl)$_2$, phenyl (unsubstituted or substituted by, for example, —OH or halogen, such as Cl, Br or especially I), —S($C_1$–$C_4$ alkyl), a 5- or 6-membered heterocyclic ring, such as, in particular, indole or imidazole, —NH—C(NH)—$NH_2$, phenoxyphenyl (unsubstituted or substituted by, for example, —OH or halogen, such as Cl, Br or especially I), an olefinic group, such as ethylene or vinyl, and CO—NH—C(NH)—$NH_2$.

Preferred substituents are lower alkyl, which here, as elsewhere in this description, is preferably $C_1$–$C_4$ allyl, $C_1$–$C_4$ alkoxy, COOH, SH, —$NH_2$, —NH($C_1$–$C_4$ alkyl), —N($C_1$–$C_4$ alkyl)$_2$ or halogen. Particular preference is given to $C_1$–$C_4$ alkyl, $C_1$–$C_4$ alkoxy, COOH and SH.

For the purposes of this invention, cycloalkyl is, in particular, cycloalkyl, and aryl is, in particular, phenyl, unsubstituted or substituted as described above.

Modifiers

The macromers can include further modifier groups and crosslinkable groups. Some such groups are described in U.S. Pat. Nos. 5,508,317, 5,665,840, 5,807,927, 5,849,841, 5,932,674, 5,939,489, and 6,011,077. Crosslinkable groups and the optional further modifier groups can be bonded to the macromer backbone in various ways, for example through a certain percentage of the 1,3-diol units being modified to give a 1,3-dioxane, which contains a crosslinkable group, or a further modifier, in the 2-position. Modifiers that might be attached to the backbone include those to modify the hydrophobicity, active agents or groups to allow attachment of active agents, photoinitiators, modifiers to enhance or reduce adhesiveness, modifiers to impart thermoresponsiveness, modifiers to impart other types of responsiveness, and additional crosslinking groups. These modifiers may be attached to the backbone, or to other monomeric units included in the backbone.

Attaching a cellular adhesion promoter to the macromers can enhance cellular attachment or adhesiveness of the biomedical articles. These agents are well known to those skilled in the art and include carboxymethyl dextran, proteoglycans, collagen, gelatin, glucosaminoglycans, fibronectin, lectins, polycations, and natural or synthetic biological cell adhesion agents such as RGD peptides.

Having pendant ester groups that are substituted by acetaldehyde or butyraldehyde acetals, for example, can increase the hydrophobicity of the macromers and the formed hydrogel. Hydrophobic groups can desirably be present in an amount from about 0 to 25%.

It may also be desirable to include in the macromer a molecule that allows visualization of the biomedical article. Examples include dyes and molecules visualizable by magnetic resonance imaging.

Degradable Regions

The macromers can form a hydrogel that is degradable. Suitable degradable systems are described in U.S. patent application Ser. No. 09/714,700, titled "Degradable Poly (Vinyl Alcohol) Hydrogels" and filed on Nov. 15, 2000. In the degradable systems described in that application, the macromers include a degradable region in the backbone or on a pendant chain. The degradable region is preferably degradable under in vivo conditions by hydrolysis. The degradable region can be enzymatically degradable. For example, the degradable region may be polymers and oligomers of glycolide, lactide, ε-caprolactone, other hydroxy acids, and other biologically degradable polymers that yield materials that are non-toxic or present as normal metabolites in the body. Preferred poly(α-hydroxy acids) are poly(glycolic acid), poly(DL-lactic acid) and poly(L-lactic acid). Other useful materials include poly(amino acids), poly(anhydrides), poly(orthoesters), poly(phosphazines), and poly (phosphoesters). Polylactones such as poly(ε-caprolactone), poly(ε-caprolactone), poly(δ-valerolactone) and poly(γ-butyrolactone), for example, are also useful. Enzymatically degradable linkages include poly(amino acids), gelatin, chitosan, and carbohydrates. The biodegradable regions may have a degree of polymerization ranging from one up to values that would yield a product that was not substantially water soluble. Thus, monomeric, dimeric, trimeric, oligomeric, and polymeric regions may be used. The biodegradable region could, for example, be a single methacrylate group.

Biodegradable regions can be constructed from polymers or monomers using linkages susceptible to biodegradation, such as ester, acetal, carbonate, peptide, anhydride, orthoester, phosphazine, and phosphoester bonds. As described therein, the biodegradable regions may be arranged within the macromers such that the formed hydrogel has a range of degradability, both in terms of extent of degradation, whether complete or partial, and in terms of time to complete or partial degradation.

Synthesis of Macromers

The macromers can be made by general synthetic methods known to those skilled in the art. The specific macromers discussed above can be made as described in U.S. Pat. Nos. 5,508,317, 5,665,840, 5,807,927, 5,849,841, 5,932,674, 5,939,489, and 6,011,077.

The specific macromers described above are extraordinarily stable. Spontaneous crosslinking by homopolymerization does not typically occur. The macromers can furthermore be purified in a manner known per se, for example by precipitation with organic solvents, such as acetone, extraction in a suitable solvent, washing, dialysis, filtration, or ultrafiltration. Ultrafiltration is especially preferred. By means of the purification process the macromers can be obtained in extremely pure form, for example in the form of concentrated aqueous solutions that are free, or at least substantially free, from reaction products, such as salts, and from starting materials.

The preferred purification process for the macromers of the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the sodium chloride content of the solution, which can be determined simply in a known manner, such as by conductivity measurements.

The macromers are crosslinkable in an extremely effective and controlled manner.

Vinylic Comonomers

The process for polymerization of the macromers may comprise, for example, crosslinking a macromer comprising units of formula I, especially in substantially pure form, that is to say, for example, after single or repeated ultrafiltration, preferably in solution, especially in aqueous solution, in the absence or presence of an additional vinylic comonomer.

The vinylic comonomer may be hydrophilic or hydrophobic, or a mixture of a hydrophobic and a hydrophilic vinylic monomer. Generally, approximately from 0.01 to 80 units of a typical vinylic comonomer react per unit of formula I, especially from 1 to 30 units per unit of formula I, and especially preferably from 5 to 20 units per unit of formula I.

If a vinylic comonomer is used, the crosslinked polymers according to the invention preferably comprise approximately from 1 to 15 percent, especially preferably approximately from 3 to 8 percent, of units of formula I or III, based on the number of hydroxy groups of the polyvinyl alcohol, which are reacted with approximately from 0.1 to 80 units of the vinylic monomer.

It is also preferable to use a hydrophobic vinylic comonomer or a mixture of a hydrophobic vinylic comonomer with a hydrophilic vinylic comonomer, the mixture comprising at least 50 percent by weight of a hydrophobic vinylic comonomer. In that manner the mechanical properties of the polymer can be improved without the water content falling substantially. In principle, however, both conventional hydrophobic vinylic comonomers and conventional hydrophilic vinylic comonomers are suitable for copolymerization with the macromer.

Suitable hydrophobic vinylic comonomers include, without the list being exhaustive, $C_1$–$C_{18}$ alkyl acrylates and methacrylates, $C_3$–$C_{18}$ alkyl acrylamides and methacrylamides, acrylonitrile, methacrylonitrile, vinyl-$C_1$–$C_{18}$ alkanoates, $C_2$–$C_{18}$ alkenes, $C_2$–$C_{18}$ haloalkenes, styrene, $C_1$–$C_6$ alkylstyrene, vinyl alkyl ethers, in which the alkyl moiety contains from 1 to 6 carbon atoms, $C_2$–$C_{10}$ perfluoroalkyl acrylates and methacrylates or correspondingly partially fluorinated acrylates and methacrylates, $C_3$–$C_{12}$ perfluoroalkyl-ethylthiocarbonylaminoethyl acrylates and methacrylates, acryloxy- and methacryloxy-alkylsiloxanes, N-vinylcarbazole, $C_3$–$C_{12}$ alkyl esters of maleic acid, fumaric acid, itaconic acid, mesaconic acid and the like. $C_1$–$C_4$ alkyl esters of vinylically unsaturated carboxylic acids having from 3 to 5 carbon atoms or vinyl esters of carboxylic acids having up to 5 carbon atoms, for example, are preferred.

Examples of suitable hydrophobic vinylic comonomers include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl) tetramethyldisiloxane.

Suitable hydrophilic vinylic comonomers include, without the list being exhaustive, hydroxy-substituted lower alkyl acrylates and methacrylates, acrylamide, methacrylamide, lower alkyl acrylamides and methacrylamides, ethoxylated acrylates and methacrylates, hydroxy-substituted lower alkyl acrylamides and methacrylamides, hydroxy-substituted lower alkyl vinyl ethers, sodium ethylenesulfonate, sodium styrenesulfonate, 2-acrylamido-2-methylpropanesulfonic acid (AMPS® monomer from Lubrizol Corporation), N-vinylpyrrole, N-vinylsuccinimide, N-vinylpyrrolidone, 2-or 4-vinylpyridine, acrylic acid, methacrylic acid, amino- (the term "amino" also including quaternary ammonium), mono-lower alkylamino- or di-lower alkylamino-lower alkyl acrylates and methacrylates, allyl alcohol and the like. Hydroxy-substituted $C_2$–$C_4$ alkyl (meth)acrylates, five- to seven-membered N-vinyl lactams, N,N-di-$C_1$–$C_4$ alkyl(meth)acrylamides and vinylically unsaturated carboxylic acids having a total of from 3 to 5 carbon atoms, for example, are preferred.

Contrast Agents

It may be desirable to include a contrast agent in the biomedical articles. A contrast agent is a biocompatible (non-toxic) material capable of being monitored by, for example, radiography. The contrast agent can be water soluble or water insoluble. Examples of water soluble contrast agents include metrizamide, iopamidol, iothalamate sodium, iodomide sodium, and meglumine. Iodinated liquid contrast agents include Omnipaque®, Visipaque®, and Hypaque-76®. Examples of water insoluble contrast agents are tantalum, tantalum oxide, barium sulfate, gold, tungsten, and platinum. These are commonly available as particles preferably having a size of about 10 μm or less.

A contrast agent can be added to the biomedical article during manufacture, so that the contrast agent is incorporated into the article. Alternatively, the article can be coated with the contrast agent.

Active Agents

An effective amount of one or more biologically active agents can be included in the biomedical articles. It may be desirable to deliver the active agent from the articles. Biologically active agents that it may be desirable to deliver include prophylactic, therapeutic, and diagnostic agents (collectively referred to herein as an "active agent" or "drug"). A wide variety of active agents can be incorporated into the hydrogel including organic and inorganic molecules and cells. Release of the incorporated additive from the hydrogel is achieved by diffusion of the agent from the hydrogel, degradation of the hydrogel, and/or degradation of a chemical link coupling the agent to the polymer. In this context, an "effective amount" refers to the amount of active agent required to obtain the desired effect.

Examples of active agents that can be incorporated include, but are not limited to, anti-angiogenic agents, chemotherapeutic agents, growth factors, nitric oxide, radiation delivery devices, such as radioactive seeds for brachytherapy, and gene therapy compositions.

Chemotherapeutic agents that can be incorporated include water soluble chemotherapeutic agents, such as cisplatin (platinol), doxorubicin (adriamycin, rubex), or mitomycin C (mutamycin). Other chemotherapeutic agents include iodinated fatty acid ethyl esters of poppy seed oil, such as lipiodol.

Cells can be incorporated into the biomedical articles, including cells to encourage tissue growth or cells to secrete a desired active agent. For example, cells that can be incorporated include fibroblasts, endothelial cells, muscle cells, stem cells, etc. Cells can be modified to secrete active agents such as growth factors.

Active agents can be incorporated into the biomedical articles simply by mixing the agent with the macromers prior to crosslinking. The active agent will then be entrapped in the hydrogel. The active agent can be in compound form or can be in the form of degradable or nondegradable nano or microspheres. It some cases, it may be possible and desirable to attach the active agent to the article after the article is formed. The active agent may also be coated onto the surface of the article. The active agent may be released from the hydrogel over time or in response to an environmental condition.

Other Additives

It may be desirable to include fillers in the biomedical articles, such as fillers that leach out of the hydrogel over a period of time and cause the hydrogel to become porous. Such may be desirable, for example, where cellular growth is desired. Appropriate fillers include calcium salts, for example.

It may be desirable to include other types of macromers in the biomedical article.

Characteristics That Can Be Modified

A number of characteristics of the hydrogel can be easily modified, making the hydrogels suitable for a number of applications. For example, as discussed above, the polymer backbones can include comonomers to add desired properties, such as, for example, thermoresponsiveness, degradability, gelation speed, and hydrophobicity. Modifiers can be attached to the polymer backbone (or to pendant groups) to add desired properties, such as, for example, thermoresponsiveness, degradability, hydrophobicity, flexibility, and adhesiveness. Active agents can also be attached to the polymer backbone using the free hydroxyl groups, or can be attached to pendant groups.

The gelation time of the compositions can be varied from about 0.5 seconds to as long as 10 minutes, and longer if desired. The gelation time will generally be affected by, and can be modified by changing at least the following variables: the initiator system, crosslinker density, macromer molecular weight, macromer concentration (solids content), and type of crosslinker. A higher crosslinker density will provide faster gelation time; a lower molecular weight will provide a slower gelation time. A higher solids content will provide faster gelation time. For redox systems the gelation time can be designed by varying the concentrations of the redox components. Higher reductant and higher oxidant will provide faster gelation, higher buffer concentration and lower pH will provide faster gelation.

The firmness of the formed hydrogel will be determined in part by the hydrophilic/hydrophobic balance, where a higher hydrophobic percent provides a firmer hydrogel. The firmness will also be determined by the crosslinker density (higher density provides firmer hydrogel), the macromer molecular weight (lower MW provides firmer hydrogel), and the length of the crosslinker (a shorter crosslinker provides a firmer hydrogel).

The swelling of the hydrogel is inversely proportional to the crosslinker density. Generally, no or minimal swelling is desired, desirably less than about 10 percent.

Elasticity of the formed hydrogel can be increased by increasing the size of the backbone between crosslinks and decreasing the crosslinker density. Incomplete crosslinking will also provide a more elastic hydrogel. In many cases, the elasticity of the hydrogel desirably substantially matches the elasticity of the tissue to which the composition is to administered or implanted.

II. Making The Hydrogel Biomedical Articles

The articles are made, in general, by dissolving macromers in an appropriate solvent, forming the macromers into a desired shape, such as by pouring the macromer solution in a mold, if desired, and crosslinking the macromers. Extrusion techniques can also be used, if desired. The macromers can also be crosslinked in contact with a substrate, such as a catheter or stent, for example, if a coating is desired.

In the case of photocrosslinking, it may be appropriate to add a photoinitiator that is capable of initiating free radical crosslinking. The crosslinking can then be initiated by actinic or ionizing radiation. An equally advantageous method of crosslinking is via redox initiation. In the case of redox initiated crosslinking, it may be appropriate to divide the prepolymer solution. The oxidizing agent of the redox initiation system is added to one part of the prepolymer solution and the reducing agent component of the redox initiation system is added to the other part. The crosslinking can then be initiated by mixing the two solutions together.

The crosslinking is carried out in a suitable solvent. Such solvents are in principle all those which dissolve the prepolymer and any vinylic comonomers additionally used, for example water, alcohols, such as lower alkanols, for example ethanol or methanol, furthermore carboxamides, such as dimethylformamide or dimethyl sulfoxide, likewise mixtures of suitable solvents, for example mixtures of water with an alcohol, for example a water/ethanol or water/methanol mixture.

In the case of photocrosslinking, it is expedient to add an initiator that is capable of initiating free-radical crosslinking and is readily soluble in water. Examples thereof are known to the person skilled in the art; suitable photoinitiators which may be mentioned specifically are benzoins, such as benzoin, benzoin ethers, such as benzoin methyl ether, benzoin ethyl ether, benzoin isopropyl ether and benzoin phenyl ether, and benzoin acetate; acetophenones, such as acetophenone, 2,2-dimethoxyacetophenone and 1,1-dichloroacetophenone; benzil, benzil ketals, such as benzil dimethyl ketal and benzil diethyl ketal, anthraquinones, such as 2-methylanthraquinone, 2-ethylanthraquinone, 2-tert-butylanthraquinone, 1-chloroanthraquinone and 2-amylanthraquinone; furthermore triphenylphosphine, benzoylphosphine oxides, for example 2,4,6-trimethylbenzoyldiphenylphosphine oxide, benzophenones, such as benzophenone and 4,4'-bis(N,N'-dimethylamino) benzophenone; thioxanthones and xanthones; acridine derivatives; phenazine derivatives; quinoxaline derivatives and 1-phenyl-1,2-propanedione 2-O-benzoyl oxime; 1-aminophenyl ketones and 1-hydroxyphenyl ketones, such as 1-hydroxycyclohexylphenyl ketone, phenyl 1-hydroxyisopropyl ketone, 4-isopropyiphenyl 1-hydroxyisopropyl ketone, 2-hydroxy-1-[4-(2-hydroxyethoxy)phenyl]-2-methylpropan-1-one, 1-phenyl-2-hydroxy-2-methylpropan-1-one, and 2,2-dimethoxy-1,2-diphenylethanone, all of which are known compounds.

Particularly suitable photoinitiators, which are usually used in combination with UV lamps as light source, are acetophenones, such as 2,2-dialkoxybenzophenones and hydroxyphenyl ketones, for example the initiators obtainable under the names Lucirin™ TPO, IRGACURE.®2959 and IRGACURE®1173.

For visible light polymerization, an initiator or photosensitizer and co-catalyst are used. Examples of suitable initiators are ethyl eosin, eosin, erythrosin, riboflavin, fluorescein, rose bengal, methylene blue, thionine, 5,7-diiodo-3-butoxy-6-fluorone, 2,4,6-trimethyl-benzoyldiphenylophosphine oxide and the like; examples of suitable co-catalysts are triethanolamine, arginine, methyldiethanol amine, triethylamine, or an organic peroxide (e.g., benzoyl peroxide) and the like. Another class of photoinitiators usually employed when argon ion lasers are used is benzil ketals, for example benzil dimethyl ketal.

The photoinitiators are added in effective amounts, expediently in amounts of from about 0.1 to about 2.0% by weight, in particular from 0.3 to 0.5% by weight, based on the total amount of the prepolymer.

The resultant solution can be introduced into a mold using methods known per se, or onto tissues or cells or onto a base material for constructing a medical device.

In a redox system employing ferrous ion, peroxide, and ascorbate, the desired amounts of the components will be determined by concerns related to gelation speed, toxicity, extent of gelation desired, and stability. Very generally, the concentration of iron will be about 20 to 1000 ppm; the concentration of hydrogen peroxide will be about 10 to 1000 ppm; the pH will be about 3 to 7; the buffer concentration will be about 10 to 200 mM; and ascorbate concentration will be about 10 to 40 mM.

In one embodiment, the biomedical articles are microparticles, such as for drug delivery. Microparticles can be made by a number of techniques known to those skilled in the art, such as single and double emulsion, suspension polymerization, solvent evaporation, spray drying, and solvent extraction. Methods for making microspheres are described in the literature, for example, in Mathiowitz and Langer, J. Controlled Release 5:13–22 (1987); Mathiowitz et al., Reactive Polymers 6:275–283 (1987); Mathiowitz et al., J. Appl. Polymer Sci. 35:755–774 (1988); Mathiowitz et al., Scanning Microscopy 4:329–340 (1990); Mathiowitz et al., J. Appl. Polymer Sci., 45:125–134 (1992); and Benita et al., J. Pharm. Sci. 73:1721–1724 (1984).

In solvent evaporation, described for example in Mathiowitz et al., (1990), Benita et al. (1984), and U.S. Pat. No. 4,272,398, the macromers are dissolved in a solvent. If desired, an agent to be incorporated, either in soluble form or dispersed as fine particles, is added to the macromer solution, and the mixture is suspended in an aqueous phase that contains a surface active agent. The resulting emulsion is stirred until most of the solvent evaporates, leaving solid microspheres, which may be washed with water and dried overnight in a lyophilizer. The microspheres are polymerized, for example, by exposure to light.

In solvent removal, the macromers are dissolved in a solvent. The mixture can then be suspended in oil, such as silicon oil, by stirring, to form an emulsion. As the solvent diffuses into the oil phase, the emulsion droplets harden into solid polymer microspheres. The microspheres can be polymerized by exposure to light, for example.

Spray drying is implemented by passing the polymerizable macromers used to form the hydrogel through a nozzle, spinning disk or equivalent device to atomize the mixture to form fine droplets. The polymerizable macromers may be provided in a solution or suspension, such as an aqueous solution. The fine droplets are exposed to light, for example, to cause polymerization of the macromer and formation of the hydrogel microspheres.

In another embodiment, hydrogel particles are prepared by a water-in-oil emulsion or suspension process, wherein the polymerizable macromers and the substance to be incorporated, if desired, are suspended in a water-in-oil suspension and exposed to light to polymerize the macromers to form hydrogel particles incorporating the substance, such as a biologically active agent.

In another embodiment, microspheres can be formed by atomizing macromer solution into oil, followed by polymerization.

There are many variables that affect the size, size distribution, and quality of the microspheres formed, such as stabilizer, stir speed, reactor geometry. An important variable is the choice of stabilizer. Good stabilizers have an HLB number from 1 to 4 and have some solubility in the oil phase. Some appropriate stabilizers include cellulose acetate butyrate (with 17% butyrate), sorbitan oleates, and dioctylsulphosuccinate. The amount and type of stabilizer will control the particle size and reduce coalescing of the particles during crosslinking. The oil can be a water-insoluble oil such as liquid paraffin, but water-insoluble halogenated solvents such as dichloroethane are commonly used. The ratio of water to oil is also important and desirably ranges from about 1:1 to 1:4.

Microspheres can be made in sizes ranging from about 10 microns to 2000 microns. In most applications it will be desirable to have a small size range of microspheres. The process used to make the microspheres can be controlled to achieve a particular desired size range of microspheres. Other methods, such as sieving, can be used to even more tightly control the size range of the microspheres.

Active agents can be included in the microspheres as described above. It may be desirable to coat the microspheres in modifiers or active agents, such as, for example, agents to increase cellular attachment. Such coating can be done by methods known to those skilled in the art.

III. Methods for Using the Hydrogel Biomedical Articles

A number of different preformed hydrogel articles can be made, such as, but not limited to, catheters, tubing, such as neural regeneration tubing, vascular grafts, heart valves, sutures, prostheses, dialysis membranes, filters, sensors, wound dressings, and drug delivery articles. The hydrogel forms all or a portion of the biomedical articles. For example, the hydrogel can form a coating on the article.

EXAMPLES

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

The following acetals were made as described in the prior art:

N-methacrylamidoacetaldehyde dimethyl acetal

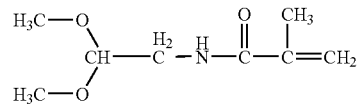

N-acrylamidoacetaldehyde dimethyl acetal

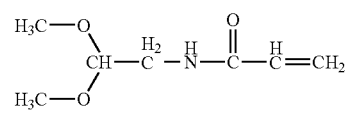

1-(2,2-Dimethoxyethyl)-3,4-dimethylpyrrole-2,5-dione

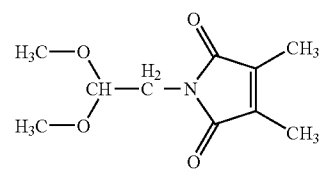

N-(2,2-Dimethoxyethyl)isobutyramide

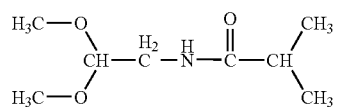

N-(2,2-Dimethoxyethyl)-3-mercaptopropionamide

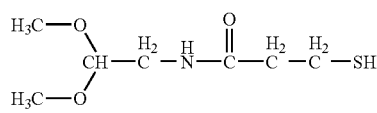

Example 1

General Method for the Preparation of High-Acetate Products of the Reaction of PVA with Acetals or Aldehydes 300 g of PVA (Mowiol 4-88, unless stated otherwise) is introduced into a 2 liter twin-jacket reactor fitted with stirrer and thermometer, 800 g of demineralized water is added, and the mixture is warmed to 95° C. with stirring.

After one hour, all the reactants have dissolved to give a clear solution, which is cooled to 20° C. A crosslinkable acetal in the amount given in the examples, if desired together with one or more acetal(s), 440 g of acetic acid, 100 g of concentrated hydrochloric acid (37%) and sufficient demineralized water to give a total of 200 g of reaction solution are added. The mixture is stirred at 20° C. for 20 hours.

Isolation can be carried out by ultrafiltration. The reaction mixture is cooled to 15° C. and the pH is adjusted to 3.6 by means of aqueous NaOH (5%). The polymer solution is filtered through a 0.45 micron filter and purified by ultrafiltration using a 1 kD Omega membrane from Filtron. The ultrafiltration is continued to a residual sodium chloride content of 0.004%. Before the purification is completed, the solution is adjusted to pH 7 using 0.1 N sodium hydroxide solution.

The isolation can also be carried out by precipitation. The reaction mixture is adjusted to pH 3.6 by means of triethylamine and precipitated in acetone in a ratio of 1:10. The precipitate is separated off, dispersed twice in ethanol and once in acetone and dried. The resultant product has the same properties as that obtained above by ultrafiltration.

Example 2

General Method for the Preparation of Low-Acetate Products of the Reaction of PVA with Acetals or Aldehydes 300 g of PVA (Mowiol 4-88, unless stated otherwise) is introduced into a 2 liter twin-jacket reactor fitted with stirrer and thermometer, 800 g of demineralized water is added, and the mixture is warmed to 95° C. with stirring. After one hour, all the reactants have dissolved to give a clear solution, which is cooled to 20° C. A crosslinkable acetal in the amount given in the examples, if desired together with one or more acetal(s), 440 g of acetic acid, 100 g of concentrated hydrochloric acid (37%) and sufficient demineralized water to give a total of 2000 g of reaction solution are added. The mixture is stirred at 20° C. for 20 hours. After 20 hours, a sample of the reaction solution is titrated with NaOH, and the degree of hydrolysis of the PVA determined. HCl is 1.034 meq/g, acetic acid is 0.265 meq/g, corresponding to a residual acetate content of 3.5 mol %. The reaction mixture is stirred at 25° C. for a further two hours and re-titrated. HCl is 1.034 meq/g, acetic acid is 0.277 meq/g, corresponding to a residual acetate content of 2.93 mol %.

The isolation can also be carried out by ultrafiltration. The reaction mixture is cooled to 15° C. and adjusted to pH 7 using aqueous NaOH (5%). The polymer solution is filtered through a 0.45 micron filter and purified by ultrafiltration using a 1 kD Omega membrane from Filtron. The ultrafiltration is continued to a residual sodium chloride content of 0.002%.

The isolation can also be carried out by precipitation. The reaction mixture is adjusted to pH 3.6 using triethylamine and precipitated in acetone in a ratio of 1:10. The precipitate is separated off, dispersed twice in ethanol and once in acetone and dried. The resultant product is comparable to that obtained above by ultrafiltration.

Examples 3a, 3b, and 3c

High Acetate Macromers

The preparation method of example 1 was used. The macromers were isolated by ultrafiltration using a 1 kD membrane (Millipore). The PVA used was Mowiol 3-83 from Hoechst, residual acetate content 17 mol %, $M_n$ 8,261, $M_n$ 3,646, $M_w/M_n$ 2.26, intrinsic viscosity [dl/g] 0.278.

3a): 30 g of acrylamidoacetaldehyde dimethyl acetal was used with 500 g of added acetic acid.

Macromer data (sol)
  Intrinsic viscosity: [dl/g] of 0.329
  N content: 0.79%
  Acetal content: 0.62 meq/g
  Acetate content: 15.3 mol %
  $M_w$ 18,500, $M_n$ 6,735, $M_w/M_n$ 2.74
  Solids content: 30% in the sol state resulted in 30.2% in the gel state.

3b): 30 g of methacrylamidoacetaldehyde dimethyl acetal was used with 500 g of added acetic acid.

Macromer data (sol)
  Intrinsic viscosity: [dl/g] of 0.282
  N content: 0.789%
  Acetal content: 0.57 meq/g
  Acetate content: 2.81 meq/g, corresponding to 15.1 mol %
  $M_w$ 14,151, $M_n$ 5652, $M_w/M_n$ 2.58
  Solids content: 30% in the sol state resulted in 30.0% in the gel state.

3c): 22.5 g of methacrylamidoacetaldehyde dimethyl acetal was used with 75.24 g HCl Macromer data (sol)
  N content: 0.676%
  Acetal content: 0.50 meq/g
  Acetate content: 1.497 meq/g, corresponding to 7.5 mol %.

Examples 3d) to 3f)

High Acetate Macromers

The preparation method of Example 1 was used. The macromers were isolated by ultrafiltration using a 5 kD membrane (Millipore). The PVA used was (Mowiol 26-88, Hoechst), residual acetate content 12 mol %.

3d): 7.0 g of acrylamidoacetaldehyde dimethyl acetal was used with 560 g of added acetic acid and 140 g of PVA.

Macromer data (sol)
  Intrinsic viscosity: [dl/g] 0.844
  N content: 0.36%
  Acetal content: 0.255 meq/g
  Acetate content: 12.8 mol %
  $M_w$ 102,341, $M_n$ 37,844, $M_w/M_n$ 2.70
  Solids content: 19.6% in the sol state resulted in 15.2% in the gel state.

3e): 14 g of acrylamidoacetaldehyde dimethyl acetal was used with 560 g of added acetic acid and 140 g of PVA.

Macromer data (sol)
  Intrinsic viscosity: [dl/g] 0.842
  N content: 0.791%
  Acetal content: 0.56 meq/g
  Acetate content: 13.4 mol %
  $M_w$ 78,214, $M_n$ 31,475, $M_w/M_n$ 2.48
  Solids content: 16.6% in the sol state resulted in 21.4% in the gel state.
  20.3% in the sol state resulted in 25.8% in the gel state.

3f): A 1:1 mixture of 15% solutions from Examples 3c) and 3d) gave a solids content of 17.3% in the gel state resulting from 15% in the sol state. A mixture of this type is suitable for adjusting the solids content and thus the shrinkage of a medical device.

Examples 4a) and 4b)

Low Acetate Macromers

The preparation method of Example 2 was used. The PVA was Mowiol 4-88 from Hoechst and the acetal was methacrylamidoacetaldehyde dimethyl acetal and modifier acetal N-(2,2-Dimethoxyethyl)isobutyramide. The reaction time was 12 hours at 20° C., isolation was by ultrafiltration.

9a): 56 g of acetal methacrylamidoacetaldehyde dimethyl acetal and 56 g of modifier acetal N-(2,2-Dimethoxyethyl) isobutyramide.

Macromer data (sol)
  N content: 2.26%
  Total acetal content: 1.61 meq/g
  Acetate content: 6.5 mol %
  Cloud point: 36° C.
  Solids content: 30% in the sol state resulted in 40.1% in the gel state.

9b): 46 g of acetal methacrylamidoacetaldehyde dimethyl acetal and 56 g of modifier acetal N-(2,2-Dimethoxyethyl) isobutyramide.

Macromer data (sol)
  N content: 2.12%
  Total acetal content: 1.52 meq/g
  Acetate content: 6.6 mol %
  Cloud point: 41° C.
  Solids content: 30% in the sol state resulted in 38.2% in the gel state.

Example 5

Production of Hydrogels via Crosslinking a) Free-radical Photocrosslinking 0.3% (based on the polymer content) of the photoinitiator Irgacure 2959 was added to a 30% solution of the macromers from Examples 3a to 4b. In a transparent polypropylene medical device mold, the solutions were exposed to a 200 W Oriel UV lamp (150 mW/cm$^2$) for 6 seconds. The hydrogels were removed from the mold. Each was a transparent solid material.

b) Photodimerization 15 g of 1-(2,2-Dimethoxyethyl)-3,4-dimethylpyrrole-2,5-dione and 30 g of conc. hydrochloric acid were added to 50 g of PVA (Mowiol 4-88, Hoechst) dissolved in 250 g of water. The mixture was stirred at 20° C. and, after 24 hours, adjusted to pH 3.6 using 5% sodium hydroxide solution. The solution was subjected to ultrafiltration through a 5 kD Millipore membrane polymer (yield 81%).

Macromer data (sol)
  Intrinsic viscosity: 0.463 [dl/g]
  N content: 1.11%
  Crosslinking agent content: 0.8 meq/g
  Acetate content: 1.9 mol %
  For crosslinking, a 30% macromer solution was sensitized by means of 5% of sodium 2-phenylquinoxaline-4-sulfonate and exposed for 5 minutes (83 mW/cm$_2$), giving a hydrogel with 6.6% expansion.

c) Thermal Crosslinking (by oxidation)

Products of the reaction of PVA (Mowiol 4-88, Hoechst) with 33.4 g of the thiol-containing acetal N-(2,2-Dimethoxyethyl)-3-mercaptopropionamide, preparation method of Example 1, isolation by ultrafiltration, 440 g of added acetic acid, no acetal crosslinking agent.

Macromer data (sol)
  Intrinsic viscosity: 0.382 [dl/g]
  Modifier content: 2.3 mol %
  Acetate content: 11.0 mol %
  GPC: $M_w$ 35,250, $M_n$ 6,934, $M_w/M_n$ 5.08.
  Solids content: Macromer is not photosensitive, crosslinks thermally.

This example clearly shows that a thiol group is a crosslinkable group.

Example 6

Microsphere Compositions

General method of making microspheres:

300 ml of 1,2-dichloroethane (DCE) or paraffin was placed into a 500 ml dented kettle and stirred with a glass stir rod. Stabilizer was added (either cellulose acetate butyrate (CAB) or dioctyl sulfosuccinate (DOS) (the percent reported is based on the amount of DCE used)) while stirring until dissolved. Once all of the stabilizer was dissolved, stirring was ceased, and nitrogen was bubbled through the solution for 10 minutes.

The macromer solution as described in Table 1 (between 10–30% solids) was placed in a 100 ml flat-bottomed flask and stirred. 0.5% potassium persulfate was added (based on amount of DCE or paraffin used) to the macromer while stirring. Once the persulfate was dissolved, nitrogen was bubbled through the solution for 5 minutes.

The macromer solution was added to the DCE or paraffin solution dropwise, while stirring at 400 rpm. Once all of the macromer solution was added, a small positive pressure of nitrogen was applied. 0.5% N,N,N,N tetramethylethylenediamine (based on amount of DCE or paraffin used) was added to the solution. The solution was lowered into an oil bath at a temperature of 55° C. and allowed to react for three hours.

After three hours, the heat was removed and stirring was continued. Once cooled, the DCE or paraffin was vacuum filtered off, and the product was washed with DCE and acetone. The product was soaked in acetone for 30 minutes, the acetone was decanted off, and the product was soaked in water for at least 30 minutes. The water was vacuum filtered off the product. The microspheres were sonicated for 30 minutes and sieved into the desired size ranges of greater than 850 microns, between 850 and 500 microns, between 500 and 250 microns, and smaller than 250 microns. The macromer used in samples A through G had a PVA backbone (14 kDa, 12% acetate incorporation) modified with 0.45 meq/g N-acrylamidoacetaldehyde dimethyl acetal pendant polymerizable groups (about 6.3 crosslinks per chain). The macromer used in sample H had a backbone of PVA 8-88 (67 kDa, 12% acetate incorporation) modified with N-acrylamidoacetaldehyde dimethyl acetal pendant polymerizable groups (about 7 crosslinks per chain). The macromer used in sample I had a backbone of PVA 4-88 (31 kDa, 12% acetate incorporation) modified with N-acrylamidoacetaldehyde dimethyl acetal pendant polymerizable groups (about 7 crosslinks per chain). The stir speed was 400 rpm except for sample G which was 350 rpm.

TABLE 3

Preparation of Microspheres

| Sample | Macromer (%) | Stabilizer | Yield (%) | Size Distribution (microns) | | | |
|---|---|---|---|---|---|---|---|
| | | | | >850 | 850–500 | 500–250 | <250 |
| A | 20 | 0.8% CAB in DCE | 101 | 0 | 3 | 80 | 17 |
| B | 20 | 0.5% CAB in DCE | 115 | 34 | 41 | 19 | 6 |
| C | 30 | 1% DOS in paraffin | 41 | nd | nd | nd | nd |
| D | 30 | 1% DOS in paraffin | 134 | 16 | 60 | 19 | 5 |
| E | 20 | 1% CAB in DCE | 96 | 0 | 14 | 72 | 13 |
| F | 20 | 0.8% CAB in DCE | 96 | 0 | 32 | 57 | 11 |
| G | 10 | 0.8% CAB in DCE | 96 | 3 | 0 | 22 | 76 |
| H | 11 | 0.8% CAB in DCE | 150 | 0 | 10 | 84 | 6 |
| I | 20 | 0.8% CAB in DCE | 92 | 6 | 60 | 31 | 3 |

The microsphere products had very little aggregates (except for sample D) and were mostly or all spherical.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A microparticle formed from macromers having a polymeric backbone comprising units having a 1,2-diol or 1,3-diol structure and at least two pendant chains bearing crosslinkable groups, wherein the crosslinkable groups are crosslinked via free radical polymerization.

2. The microparticle of claim 1, wherein the backbone polymer comprises poly(vinyl alcohol) (PVA) and copolymers thereof.

3. The microparticle of claim 1, wherein the macromer has the formula:

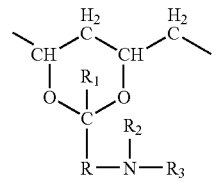

in which R is a linear or branched $C_1$–$C_8$ alkylene or a linear or branched $C_1$–$C_{12}$ alkane; $R_1$ is hydrogen, a $C_1$–$C_6$ alkyl, or a cycloalkyl; $R_2$ is hydrogen or a $C_1$–$C_6$ alkyl; and $R_3$ is an olefinically unsaturated electron attracting copolymerizable radical having up to 25 carbon atoms.

4. The microparticle of claim 1, further comprising an active agent.

5. The microparticle of claim 4, wherein the microparticle releases the active agent over a period of time ranging from about 1 day to 6 months.

6. The microparticle of claim 1, wherein the microparticle is biodegradable.

7. The microparticle of claim 1, further comprising a contrast agent.

8. The microparticle of claim 1, wherein the crosslinkable groups are crosslinked via free radical polymerization.

9. The microparticle of claim 1, wherein the free radical polymerization is redox initiated.

* * * * *